(12) United States Patent
Ogura et al.

(10) Patent No.: US 10,231,603 B2
(45) Date of Patent: Mar. 19, 2019

(54) CONNECTOR

(71) Applicant: FUJIFILM Corporation, Tokyo (JP)

(72) Inventors: Ryosuke Ogura, Kanagawa (JP);
Kimitake Fukushima, Kanagawa (JP);
Kazuyoshi Hara, Kanagawa (JP);
Kunihiko Tanaka, Kanagawa (JP);
Koji Yoshida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 369 days.

(21) Appl. No.: 15/168,079

(22) Filed: May 29, 2016

(65) Prior Publication Data
US 2016/0367115 A1 Dec. 22, 2016

(30) Foreign Application Priority Data

Jun. 17, 2015 (JP) .................. 2015-122439

(51) Int. Cl.
*A61B 1/00* (2006.01)

(52) U.S. Cl.
CPC ...... *A61B 1/00121* (2013.01); *A61B 1/00016* (2013.01); *A61B 1/00029* (2013.01)

(58) Field of Classification Search
CPC ............ A61B 1/00121; A61B 1/00016; A61B 1/00029; A61B 1/00114; A61B 1/00124
USPC ........................................................ 600/132
See application file for complete search history.

(56) References Cited

U.S. PATENT DOCUMENTS

| 4,537,453 A | 8/1985 | Takeuchi |
| 4,755,873 A * | 7/1988 | Kobayashi ............. A61B 1/042 348/74 |
| 6,141,037 A * | 10/2000 | Upton ................ A61B 1/00016 128/908 |

(Continued)

FOREIGN PATENT DOCUMENTS

| JP | 2002258100 | 9/2002 |
| JP | 2007-097691 | 4/2007 |

(Continued)

OTHER PUBLICATIONS

"Office Action of Japan Counterpart Application," dated May 2, 2018, with English translation thereof, p. 1-p. 8.

(Continued)

*Primary Examiner* — Timothy J Neal
*Assistant Examiner* — Jae Woo
(74) *Attorney, Agent, or Firm* — JCIPRNET

(57) ABSTRACT

There is provided a connector for an endoscope that is easy to grip and is easily connected to a light source device. The connector includes: a light guide part, a wireless communication unit, a wireless power receiving unit, a housing section which houses the wireless communication unit and the wireless power receiving unit and in which the light guide part protrudes from a front surface thereof positioned close to a light source device in a connection posture where the connector is connected to the light source device, and a grip section that includes a concave finger placing portion on which a thumb is placed and which is provided on an upper surface thereof on a central axis of the light guide part in a case in which the grip section is viewed from an upper surface of the connector positioned on a vertically upper side in the connection posture.

20 Claims, 7 Drawing Sheets

(56) References Cited

U.S. PATENT DOCUMENTS

| | | | |
|---|---|---|---|
| 6,699,181 B2* | 3/2004 | Wako | A61B 1/07 600/132 |
| 6,960,161 B2* | 11/2005 | Amling | A61B 1/00119 600/110 |
| 8,187,175 B2 | 5/2012 | Yoshimitsu et al. | |
| 8,568,301 B2* | 10/2013 | Watanabe | A61B 1/00121 439/180 |
| 8,617,055 B2* | 12/2013 | Kanno | A61B 1/00059 600/109 |
| 9,028,122 B2* | 5/2015 | Tuchrelo | H01R 13/7175 362/253 |
| 9,160,118 B2* | 10/2015 | Tuchrelo | H01R 13/665 |
| 9,437,987 B1* | 9/2016 | Yang | H01R 24/58 |
| 9,762,008 B2* | 9/2017 | Burris | H01R 9/05 |
| 9,986,894 B2* | 6/2018 | Shimobayashi | G02B 23/24 |
| 2002/0099265 A1* | 7/2002 | Wako | A61B 1/07 600/132 |
| 2003/0235374 A1 | 12/2003 | Luther et al. | |
| 2004/0157499 A1* | 8/2004 | Nania | H01R 13/6271 439/680 |
| 2006/0018605 A1 | 1/2006 | Luther et al. | |
| 2006/0052663 A1* | 3/2006 | Koitabashi | A61B 1/00121 600/132 |
| 2006/0116550 A1* | 6/2006 | Noguchi | A61B 1/015 600/132 |
| 2006/0116552 A1* | 6/2006 | Noguchi | A61B 1/00121 600/159 |
| 2006/0173245 A1* | 8/2006 | Todd | A61B 1/0653 600/178 |
| 2008/0188756 A1* | 8/2008 | Fujimura | A61B 8/12 600/459 |
| 2009/0216086 A1* | 8/2009 | Omori | A61B 1/00114 600/178 |
| 2010/0305400 A1* | 12/2010 | Onoda | A61B 1/00062 600/104 |
| 2011/0184244 A1* | 7/2011 | Kagaya | A61B 1/00117 600/182 |
| 2011/0193948 A1* | 8/2011 | Amling | A61B 1/00006 348/68 |
| 2012/0202385 A1* | 8/2012 | Miyagi | A61B 1/00124 439/626 |
| 2013/0035550 A1* | 2/2013 | Watanabe | G02B 6/4298 600/132 |
| 2013/0141557 A1* | 6/2013 | Kawata | A61B 1/00006 348/65 |
| 2014/0094656 A1* | 4/2014 | Matsukawa | G02B 23/2476 600/110 |
| 2014/0155696 A1* | 6/2014 | Sakata | A61B 1/0055 600/138 |
| 2014/0309491 A1* | 10/2014 | Karasawa | A61B 1/00124 600/103 |
| 2015/0045614 A1* | 2/2015 | Krivopisk | A61B 1/00121 600/103 |
| 2015/0057500 A1* | 2/2015 | Salman | A61B 1/00006 600/132 |
| 2016/0089000 A1* | 3/2016 | Hara | A61B 1/00013 600/112 |
| 2016/0089001 A1* | 3/2016 | Hara | A61B 1/00013 600/109 |
| 2016/0220095 A1* | 8/2016 | Shimomura | A61B 1/00006 |
| 2016/0367115 A1* | 12/2016 | Ogura | A61B 1/00121 |
| 2016/0367116 A1* | 12/2016 | Ogura | A61B 1/00121 |
| 2017/0014019 A1* | 1/2017 | Ogura | A61B 1/00126 |
| 2017/0273545 A1* | 9/2017 | Dong | A61B 1/008 |
| 2017/0303772 A1* | 10/2017 | Shimobayashi | G02B 23/24 |
| 2018/0185004 A1* | 7/2018 | Saiga | A61B 1/06 |

FOREIGN PATENT DOCUMENTS

| | | |
|---|---|---|
| JP | 2008-043450 | 2/2008 |
| JP | 2010049287 | 3/2010 |
| JP | 2012-125401 | 7/2012 |
| JP | 2013-013648 | 1/2013 |
| JP | 2013-158425 | 8/2013 |
| JP | 2013-208187 | 10/2013 |
| JP | 2014071397 | 4/2014 |
| WO | 2005077249 | 8/2005 |
| WO | 2011052408 | 5/2011 |

OTHER PUBLICATIONS

"Office Action of Japan Counterpart Application," with machine English translation thereof, dated Jul. 25, 2018, p. 1-p. 4.

* cited by examiner

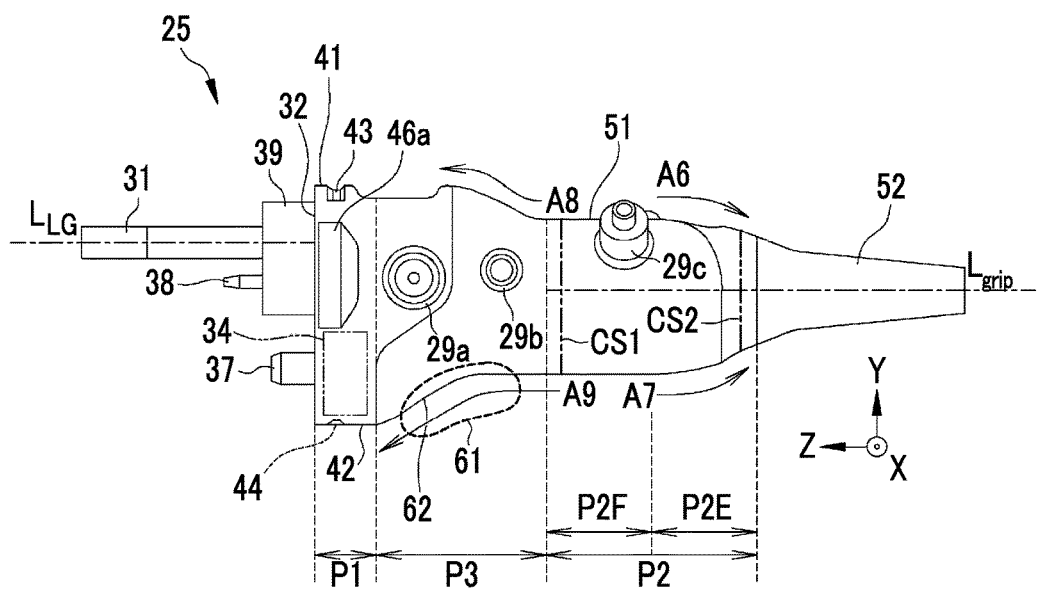
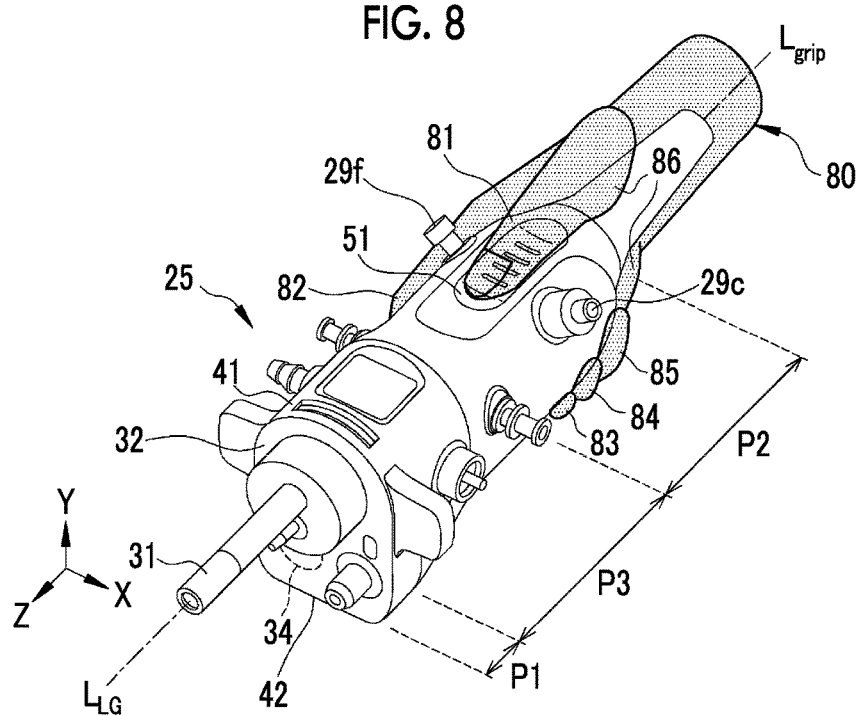

CONNECTOR

CROSS-REFERENCE TO RELATED APPLICATIONS

The present application claims priority under 35 U.S.C. § 119 to Japanese Patent Application No. 2015-122439, filed on Jun. 17, 2015. Each of the above application(s) is hereby expressly incorporated by reference, in its entirety, into the present application.

BACKGROUND OF THE INVENTION

1. Field of the Invention

The present invention relates to a connector of an endoscope that is connected to a light source device generating illumination light.

2. Description of the Related Art

A diagnosis, which uses an endoscope system including an endoscope, a light source device, and a processor device, is generally made in a medical field. The endoscope includes an insertion part that is inserted into a subject, and images an observation object (a mucous membrane or the like present in the subject) that is irradiated with illumination light generated by the light source device. The processor device generates the image of the observation object by using image signals that are obtained from the imaging of the observation object, and displays the image of the observation object in a monitor.

The endoscope is connected to the light source device and the processor device by a cable that is called a universal cable. The universal cable extends from an operation part (a grip section) of the endoscope, and a connector, which is to be connected to the light source device and the processor device, is provided at an end portion of the universal cable. In a system in which a light source device and a processor device are separately formed as in endoscope systems disclosed in JP2008-043450A and JP2012-125401A, a connector includes a connector (hereinafter, referred to as an optical connector) from which a light guide (a light guide part) for guiding illumination light generated by the light source device protrudes and which allows insertion of the light guide into the light source device to optically connect the light guide to the light source device, and a connector (hereinafter, referred to as an electrical connector) that is electrically connected to the processor device by an electrical contact for sending and receiving control signals, image signals obtained from imaging performed by the endoscope, and the like. For example, the electrical connector is provided so as to branch from the optical connector. Further, a connector in which an optical connector and an electrical connector are integrated with each other is used in a system in which a light source device and a processor device are integrated with each other as in JP2013-208187A, JP2013-158425A, and JP2007-097691A.

Furthermore, there is a case in which the connector is provided with a wireless sending portion for wirelessly sending image signals and a power receiving portion for receiving power to be supplied in a non-contact manner (JP2013-208187A).

SUMMARY OF THE INVENTION

As in JP2008-043450A, JP2012-125401A, JP2013-208187A, JP2013-158425A, JP2007-097691A, and JP2013-013648A, the light guide (an end portion of an unbundled optical fiber in JP2013-013648A) protrudes from the end face of the connector for the endoscope. For this reason, when the connector is to be connected to the light source device, there is a case in which the light guide is damaged by colliding with the light source device without being correctly inserted into a hole of the light source device into which the light guide is to be inserted according to the direction, the angle, or the like of the connector. Accordingly, when connecting the connector to the light source device, it is necessary to carefully connect the connector to the light source device while checking whether or not a connection position and an angle are correct.

When the light guide is damaged, a defect in which the observation object is darkened or the like is generated due to the deterioration of the efficiency of the guiding of illumination light. Accordingly, in recent years, a connector has been required to be formed in a shape that is easier to grip than the connector in the related art so that the connector is easily connected to the light source device.

For example, since the connectors disclosed in JP2008-043450A and JP2012-125401A can be gripped at substantially an arbitrary orientation and angle without having a designated manner of gripping, the orientation and angle of the connector with respect to the light source device needs to be adjusted by changing the grip or the like of the connector whenever the connector is connected to the light source device. For this reason, in the cases of the connectors disclosed in JP2008-043450A and JP2012-125401A, there is room for making the connector able to be more easily gripped for easy connection of the connector to the light source device.

Each of the connectors disclosed in JP2013-208187A, JP2013-158425A, and JP2007-097691A has the shape of a rectangular parallelepiped of which a tip portion close to the light source device is large, and has an L shape where a portion to be connected to the universal cable protrudes from the tip portion of the rectangular parallelepiped. Further, considering positions where slip stoppers are provided and considering that connection terminals to be connected to a water supply tank and the like provided in the vicinity thereof protrude, a root portion formed to be thin needs to be held by being picked up from the upper and lower sides. For this reason, since the root portion is unstable, it is difficult to accurately control a position where the light guide is inserted. Further, a method of gripping a large rectangular parallelepiped-shaped portion, which is close to the light source device, from the left and right sides to hold an L-shaped connector has also been considered, but it is difficult to accurately control the position of the light guide in the vertical direction and the insertion angle of the light guide in this method.

Furthermore, notches are formed on the outer surface of the cylindrical connector disclosed in JP2013-013648A, but the surface on which the notches are formed are the side surfaces of the connector. For this reason, in a case in which the connector is naturally held using the notches, the connector is picked up by fingers so as to be covered from the upper surface and is held in a direction perpendicular to the arm. Accordingly, considering the movable range of a wrist, or the like, it is difficult to connect the connector while positioning the light source device in front and checking a connection position.

An object of the invention is to provide a connector that is easier to grip than a connector in the related art and is easily connected to a light source device.

There is provided a connector for an endoscope that is connected to a light source device generating illumination light. The connector comprises a light guide part that guides the illumination light, a wireless communication unit that wirelessly communicates with the light source device, a wireless power receiving unit that receives power wirelessly supplied from the light source device, a housing section which houses the wireless communication unit and the wireless power receiving unit and in which the light guide part protrudes from a front surface thereof positioned close to the light source device in a connection posture where the connector is connected to the light source device, a grip section that includes a concave finger placing portion on which a thumb is placed and which is provided on a central axis of the light guide part in a case in which the grip section is viewed from above an upper surface of the connector positioned on a vertically upper side in the connection posture, and a finger locking portion that is provided between the housing section and the grip section and locks a forefinger on a lower surface of the connector and on the rear of the wireless power receiving unit in the connection posture.

It is preferable that a central axis of the grip section is coincident with a central axis of the light guide part in a case in which the connector is viewed from the upper surface thereof in the connection posture.

It is preferable that the central axis of the light guide part is offset to the upper surface of the connector in the connection posture with respect to the central axis of the grip section.

It is preferable that the housing section is capable of housing the wireless communication unit and the wireless power receiving unit on a side thereof close to a lower surface of the connector positioned on a vertically lower side in the connection posture.

It is preferable that the grip section has a shape in which a cross-sectional area decreases toward a rear portion thereof opposite to the housing section from a front portion thereof, which is close to the housing section, in the connection posture.

It is preferable that a lower surface of the housing section, which is positioned on the vertically lower side in the connection posture, is a flat surface.

It is preferable that an upper surface of the housing section, which is positioned on the vertically upper side in the connection posture, is a curved surface.

It is preferable that the wireless communication unit is capable of performing near-infrared communication between the light source device and itself.

It is preferable that a front surface of the connector where the wireless power receiving unit receives power supplied from the light source device has a structure in which a gap is formed between the front surface of the connector and a contact surface of the light source device in a case in which the connector is connected to the light source device.

It is preferable that the housing section houses the wireless power receiving unit so that the wireless power receiving unit comes into contact with the upper surface of the connector in the connection posture and the wireless power receiving unit receives power supplied from the light source device through the upper surface of the connector in the connection posture.

It is preferable that in a case in which the light source device includes an upper flange portion that holds the upper surface of the connector in the connection posture and the wireless power receiving unit is capable of receiving power to be supplied through the upper flange portion.

It is preferable that the central axis of the light guide part is coincident with the central axis of the grip section in a case in which the connector is viewed from a left side surface or a right side surface thereof in the connection posture.

The connector of the invention is easier to grip than a connector in the related art and is easily connected to a light source device.

BRIEF DESCRIPTION OF THE DRAWINGS

FIG. 4 is a front view of the connector that is placed on a table or the like.

FIG. 7 is a side view of the connector.

FIG. 8 is a perspective view of the connector that is gripped with the right hand.

DESCRIPTION OF THE PREFERRED EMBODIMENTS

Figure 1:
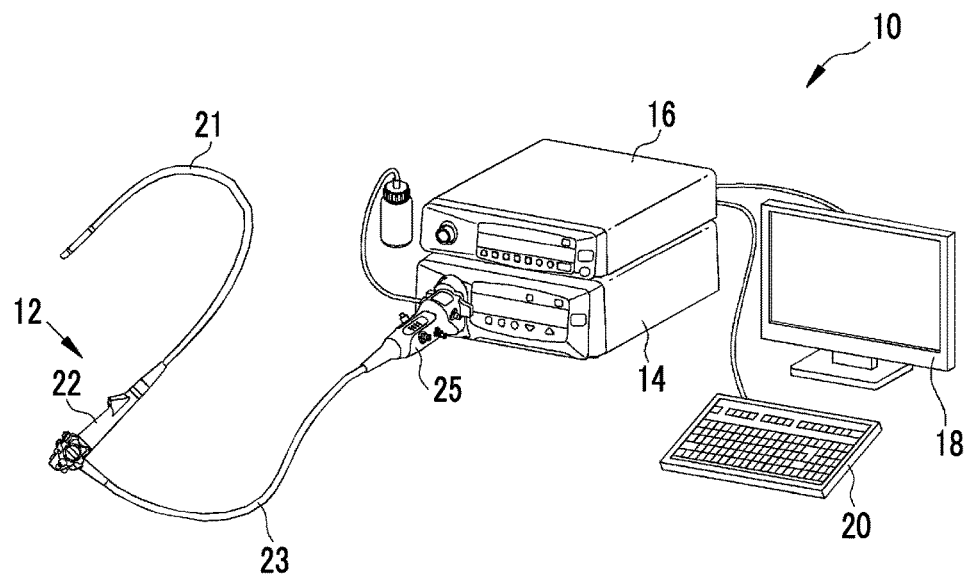
FIG. 1 is a view showing the appearance of an endoscope system.

As shown in FIG. 1, an endoscope system 10 includes an endoscope 12, a light source device 14, a processor device 16, a monitor 18, and a console 20. The endoscope 12 includes an insertion part 21 that is inserted into a subject, an operation part 22 that is provided at the base end portion of the insertion part 21, and a universal cable 23. The universal cable 23 is a cable in which a light guide part 31 (see FIG. 2) for guiding illumination light emitted from the light source device 14, a control line for controlling an imaging sensor provided at the tip of the insertion part 21, a signal line for sending image signals output from the imaging sensor during the imaging of an observation object irradiated with the illumination light, a power line for supplying power to each part such as the imaging sensor, and the like are integrated with each other. The universal cable 23 extends from the base end portion of the operation part 22, and a connector 25 connected to the light source device 14 is provided at the tip of the universal cable 23. Further, the light guide part 31 of the endoscope 12 is a light guide that is a bundle of optical fibers.

The light source device 14 generates illumination light by a semiconductor light source, such as a LED (Light Emitting Diode) or a LD (Laser Diode), or a halogen lamp such as a xenon lamp. In a case in which the connector 25 is connected to the light source device 14, illumination light is incident on the light guide part 31 of the connector 25 and is applied to an observation object from the tip of the insertion part 21.

Further, the light source device 14 is electrically connected to the processor device 16, and the connector 25 of the endoscope 12 is connected to the processor device 16 through the light source device 14. The sending and receiving of control signals, image signals, and the like between the light source device 14 and the connector 25 are wireless communication. For this reason, the light source device 14 transmits control signals and the like, which are wirelessly sent to and received from the connector 25, to the processor device 16. Furthermore, the light source device 14 supplies power, which is used to drive the imaging sensor and the like, to the connector 25, but the supply of this power is also performed wirelessly.

The processor device 16 controls the amount and light emitting timing of illumination light emitted from the light source device 14, the operation of the imaging sensor, and the like, and generates an endoscopic image by using image signals that are obtained from the imaging of the observation object that is irradiated with the illumination light. Further, the processor device 16 is electrically connected to the monitor 18 and the console 20. The monitor 18 displays the endoscopic image generated by the processor device 16, information about the endoscopic image, and the like. The console 20 is a user interface that receives an input operation, such as function setting.

Figure 2:
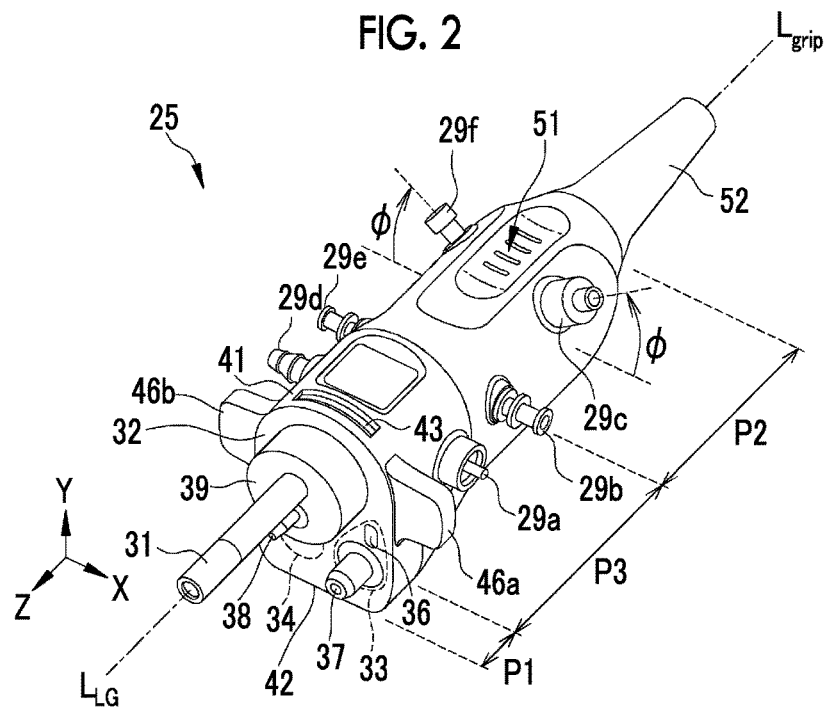
FIG. 2 is a perspective view showing the appearance of a connector.

As shown in FIG. 2, the connector 25 includes a housing section P1, a grip section P2, and an intermediate section P3. Further, the connector 25 includes a plurality of connection terminals 29a to 29f that are connected to devices and the like other than the light source device 14. Hereinafter, a posture where the connector 25 is correctly connected to the light source device 14 arranged horizontally is referred to as a "connection posture", a connection direction in which the connector 25 is connected to the light source device 14 in the connection posture is referred to as a Z direction, the vertical direction of the connector 25 in the connection posture is referred to as a Y direction, and a direction, which is in a horizontal plane perpendicular to the Z direction and the Y direction, is referred to as an X direction. The positive side in the Z direction is a side where the light source device 14 is positioned when viewed from the connector 25; the positive side in the Y direction is a vertically upper side; and the positive side in the X direction is a left side when viewed toward the positive side from the negative side in the Z direction.

In this case, the surface of the connector 25 in the connection posture, which is viewed from the vertically upper side, is an upper surface 41 and the surface of the connector 25 in the connection posture, which is viewed from the vertically lower side, is a lower surface 42. The surface of the connector 25 in the connection posture, which is viewed from the positive side in the X direction, is a left side surface, and the surface of the connector 25 in the connection posture, which is viewed from the negative side in the X direction, is a right side surface. The surface of the connector 25 in the connection posture, which is viewed from the positive side in the Z direction, is a front surface (or the front), and the surface of the connector 25 in the connection posture, which is viewed from the negative side in the Z direction, is a rear surface (or the back).

The housing section P1 houses a wireless communication unit 33 that wirelessly communicates with the light source device 14 and a wireless power receiving unit 34 that wirelessly receives power supplied from the light source device 14, and the light guide part 31 protrudes from the front surface 32 that is positioned close to the light source device 14 in the connection posture. Since a position at which the light guide part 31 protrudes is close to the upper surface 41 that is positioned on the vertically upper side in the connection posture, the housing section P1 houses the wireless communication unit 33 and the wireless power receiving unit 34 on a side thereof close to the lower surface 42 positioned on the vertically lower side in the connection posture.

The front surface 32 is a surface on an XY plane perpendicular to the Z direction and is also a tip surface of the connector 25. A pump connection portion 38 protrudes from the front surface 32 on the vertically lower side of the light guide part 31 in addition to the light guide part 31. A pump (not shown), which is provided in the light source device 14, is connected to the pump connection portion 38 when the connector 25 is connected to the light source device 14. Further, the pump connection portion 38 is connected to a conduit, such as an air/water supply channel, communicating with the connector 25, the universal cable 23, the operation part 22, and the insertion part 21. Furthermore, a fitting protrusion 39, which is fitted to a fitting recess 111 (see FIG. 10) provided on the light source device 14, is provided at the base end portion of the light guide part 31 and the pump connection portion 38, and the fitting protrusion 39 also protrudes from the front surface 32. Since the light guide part 31 protrudes in the Z direction so as to be longer than the fitting protrusion 39, the light guide part 31 is visible when a user grips the connector 25. A central axis $L_{LG}$ of the light guide part 31 and the protruding direction of the pump connection portion 38 are parallel to the Z direction.

Figure 3:
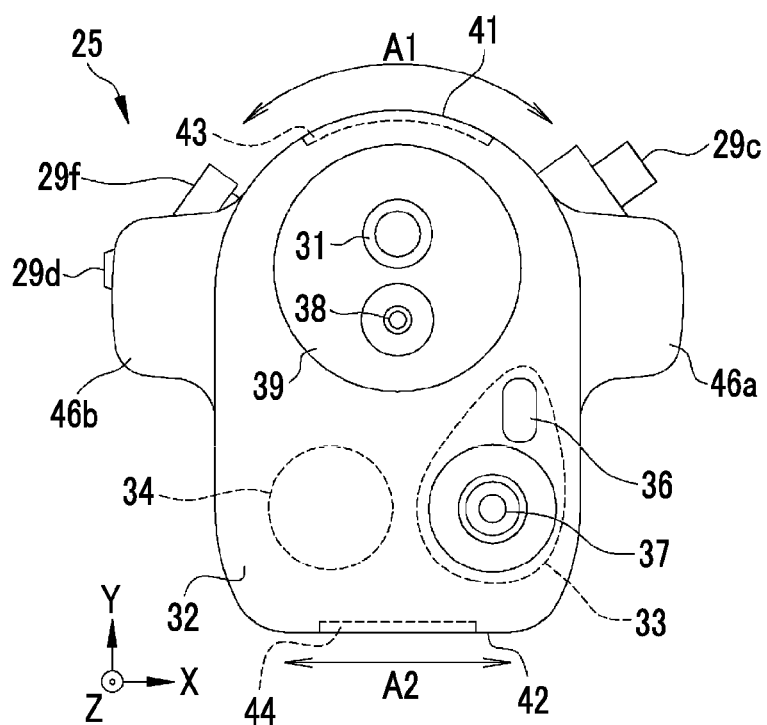
FIG. 3 is a front view of the connector.

As shown in FIG. 3, the light guide part 31 and the pump connection portion 38 are disposed in the laterally middle of the front surface 32 so as to be lined up in the Y direction. Further, the upper surface 41 of the housing section P1, which is positioned on the vertically upper side in the connection posture, is a curved surface as shown by an arrow A1, and the lower surface 42 of the housing section P1, which is positioned on the vertically lower side in the connection posture, is a flat surface as shown by an arrow A2. More specifically, the housing section P1 has a so-called "hog-backed shape". That is, the upper surface 41 of the housing section P1 has the shape of a circular arc convex toward the positive side in the Y direction in a case in which the upper surface 41 is viewed from the front surface 32, and has a shape maintaining a substantially constant height in the Z direction in a case in which the upper surface 41 is viewed from the right side surface or the left side surface. The light guide part 31 and the pump connection portion 38 are provided on the front surface 32 so as to be close to the upper surface 41. In contrast, the wireless communication unit 33 and the wireless power receiving unit 34 are provided on the front surface 32 so as to be close to the lower surface 42 and be lined up laterally.

The wireless communication unit 33 includes: a control signal sending/receiving part 36 that wirelessly sends and receives control signals, which control the light source device 14, the imaging sensor, and the like, to and from the light source device 14; and an image signal sending part 37 that wirelessly sends image signals, which are obtained from the imaging of the observation object irradiated with the illumination light, to the light source device 14. Wireless communication, which is performed by the control signal sending/receiving part 36 and the image signal sending part 37, is optical communication, and it is preferable that the wireless communication is, for example, near-infrared communication using near-infrared light (light having a wavelength in the range of about 0.7 µm to 2.5 µm). A connection terminal of the control signal sending/receiving part 36 is formed substantially on the front surface 32, and a connection terminal of the image signal sending part 37 protrudes from the front surface 32 in parallel with the Z direction.

The wireless power receiving unit 34 is, for example, a coil (a so-called secondary coil), and receives power that is supplied from a coil (a so-called primary coil) of the light source device 14 by a non-contact power transmission method, such as an electromagnetic induction method or a magnetic field resonance method. In this case, since the wireless power receiving unit 34 is provided on the rear of the front surface 32, the wireless power receiving unit 34 receives power supplied from the light source device 14 through the front surface 32. The wireless power receiving unit 34 supplies power to each part of the endoscope 12 such as the imaging sensor.

When the connector 25 is connected to the light source device 14, the light source device 14 locks the connector 25 at the upper surface 41 and the lower surface 42 of the housing section P1. Accordingly, the light source device 14 locks the connector 25 and maintains connection. For this purpose, the light source device 14 is provided with locking members 108 (see FIG. 10), which are used to lock the connector 25, at the positions thereon corresponding to the upper surface 41 and the lower surface 42 of the housing section P1. So as to correspond to the locking members 108, a groove 43 to which the locking members 108 of the light source device 14 are fitted is provided on the upper surface 41 of the connector 25 and a groove 44 to which the locking members of the light source device 14 are fitted is provided on the lower surface 42 of the connector 25.

Figure 4:
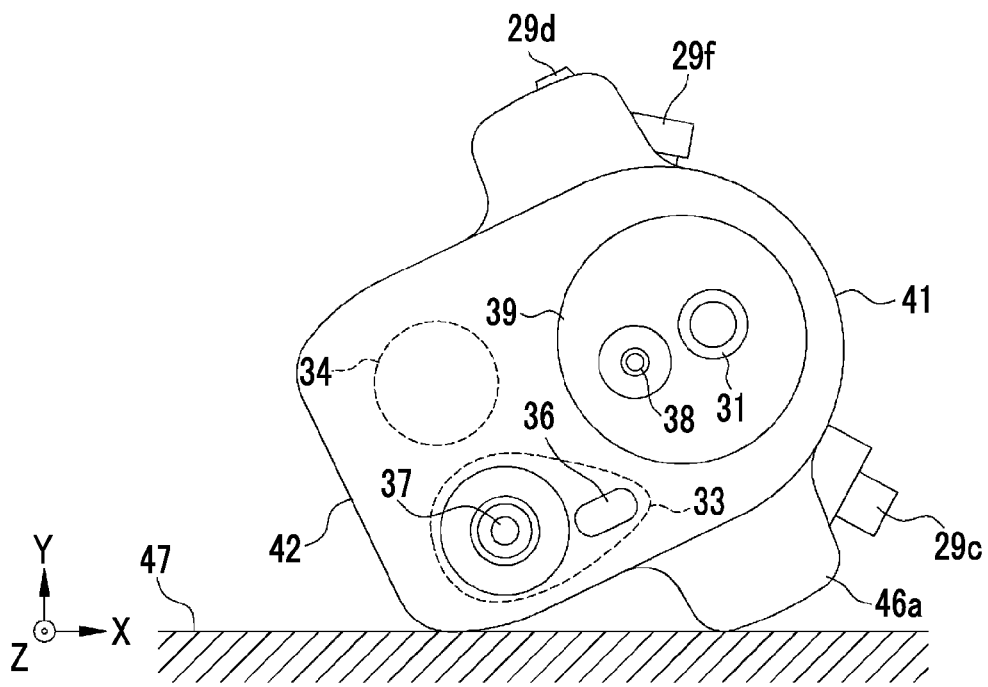

Further, a left ear portion 46a, which protrudes toward the positive side in the X direction, is provided on the left side surface of the housing section P1, and a right ear portion 46b, which protrudes toward the negative side in the X direction, is provided on the right side surface of the housing section P1. That is, the housing section P1 includes the left and right ear portions 46a and 46b, which protrude in the horizontal direction, on the side surfaces thereof between the upper and lower surfaces 41 and 42. Even though the connector 25 tilts when the connector 25 is placed on a table 47 or the like, the left ear portion 46a prevents the connection terminals 29a to 29c, which are provided on the left side surface of the connector 25, from colliding with the table 47 or the like as shown in FIG. 4. Likewise, even though the connector 25, which is placed on the table 47 or the like, tilts, the right ear portion 46b prevents the connection terminals 29d to 29f, which are provided on the right side surface of the connector 25, from colliding with the table 47 or the like. Meanwhile, since the lower surface 42 of the housing section P1 of the connector 25 is a flat surface, it is difficult for the connector 25 to tilt in comparison with a case in which the lower surface 42 is a curved surface.

The grip section P2 is a rear end (a portion corresponding to the negative side in the Z direction) of the connector 25, and is a portion that is gripped by a user in a case in which the user connects the connector 25 to the light source device 14 and a case in which the user removes the connector 25 from the light source device 14. A concave finger placing portion 51 on which the user places his thumb when gripping the connector 25 is provided on the upper surface 41 of the grip section P2.

Figure 5:
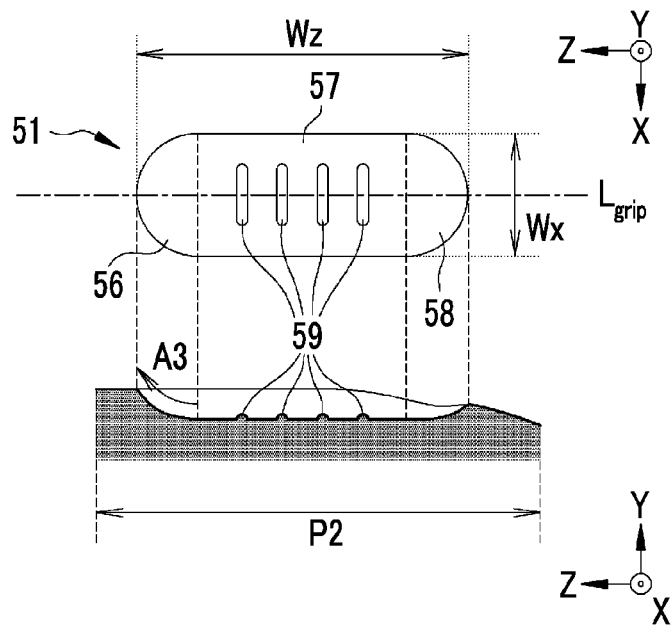
FIG. 5 shows a top view and a sectional view of a finger placing portion.

In a case in which the connector 25 is viewed from above the upper surface 41, as shown in FIG. 5, the finger placing portion 51 includes a semi-circular front portion 56 that is close to the housing section P1, a rectangular middle portion 57 of which the longitudinal direction is parallel to the Z direction, and a semi-circular rear portion 58 that is close to the universal cable 23; and is a stadium-shaped recess of which a length Wz in a direction (a first direction) parallel to a central axis $L_{grip}$ of the grip section P2 is longer than a length Wx in a direction (a second direction) orthogonal to the central axis $L_{grip}$ of the grip section P2. The surface of the front portion 56, which is close to the housing section P1, of the finger placing portion 51 is formed of a curved surface, and the front portion 56 is formed in a shape that gradually becomes shallow toward the housing section P1 from the middle portion 57 and the rear portion 58, which are provided on the side opposite to the housing section P1, as shown by an arrow A3. For this reason, the depth of the front portion 56 is reduced toward the housing section P1 from the rear portion 58 (or the middle portion 57). Further, the depth of the front portion 56 of the finger placing portion 51 is reduced as being distant from the middle even when viewed in the X direction. That is, the front portion 56 of the finger placing portion 51 is formed in a shape that fits the shape of the tip of the thumb placed on the finger placing portion 51. Meanwhile, the depth of the front portion 56, the middle portion 57, the rear portion 58, or the finger placing portion 51 is a depth from the upper surface 41 around the finger placing portion 51.

Slip stoppers 59 are formed on the middle portion 57 of the finger placing portion 51. The slip stoppers 59 are elongated stadium-shaped protrusions that are parallel to the X direction. When a thumb is placed on the finger placing portion 51, the slip stoppers 59 generate a force resistant to the belly (a portion of the thumb on which fingerprints are formed) of the thumb in the Z direction. For this reason, it is difficult for the thumb placed on the finger placing portion 51 to slip even though a force is applied in the Z direction in a case in which the connector 25 is connected to the light source device 14 or a case in which the connector 25 is removed from the light source device 14. Further, since the middle portion 57 of the finger placing portion 51 has a depth substantially constant in the Z direction but has the shape of a U-shaped surface curved in the X direction, the thumb is naturally placed in the middle of the finger placing portion 51 when the thumb is placed on the finger placing portion 51.

Similar to the front portion 56, the rear portion 58 of the finger placing portion 51 is formed of a curved surface. However, on the contrary to the front portion 56, the shape of the surface of the rear portion 58 becomes shallow from the middle portion 57 toward the rear end of the connector 25 to which the universal cable 23 is connected, and becomes shallow as being distant from the middle when viewed in the X direction.

Further, the entire shape of the grip section P2 is formed substantially in the shape of a cylinder that has a thickness easy to grip, and the universal cable 23 is connected to a rear portion P2E of the grip section P2. A cover 52 covers a connection portion between the grip section P2 and the universal cable 23, so that the rear portion P2E of the grip section P2 and the universal cable 23 are smoothly connected to each other. Furthermore, a front portion P2F of the grip section P2 has a substantially constant thickness. As shown by arrows A4 and A5 of FIG. 6 and arrows A6 and A7 of FIG. 7, the rear portion P2E of the grip section P2 becomes narrow toward the rear portion where the universal cable 23 is positioned. That is, the grip section P2 has a shape where a cross-sectional area is reduced toward the rear portion P2E thereof opposite to the housing section P1 from the front portion P2F thereof, which is close to the housing section P1, in the connection posture. Further, the cross-section of the grip section P2, which is perpendicular to the central axis $L_{grip}$, has a substantially circular shape regardless of a position in the Z direction. More specifically, the front portion P2F of the grip section P2 has a substantially constant cross-sectional area, and the cross-sectional area of the rear portion P2E of the grip section P2 is reduced toward the negative side in the Z direction where the universal cable 23 is connected. For example, when a cross-section CS1 shown in the front portion P2F by a two-dot chain line is compared with a cross-section CS2 shown in the rear portion P2E by a two-dot chain line, all of the cross-sections CS1 and CS2 have a substantially circular shape but the area of the cross-section CS2 of the rear portion P2E is smaller than the area of the cross-section CS1 of the front portion P2F.

Figure 6:
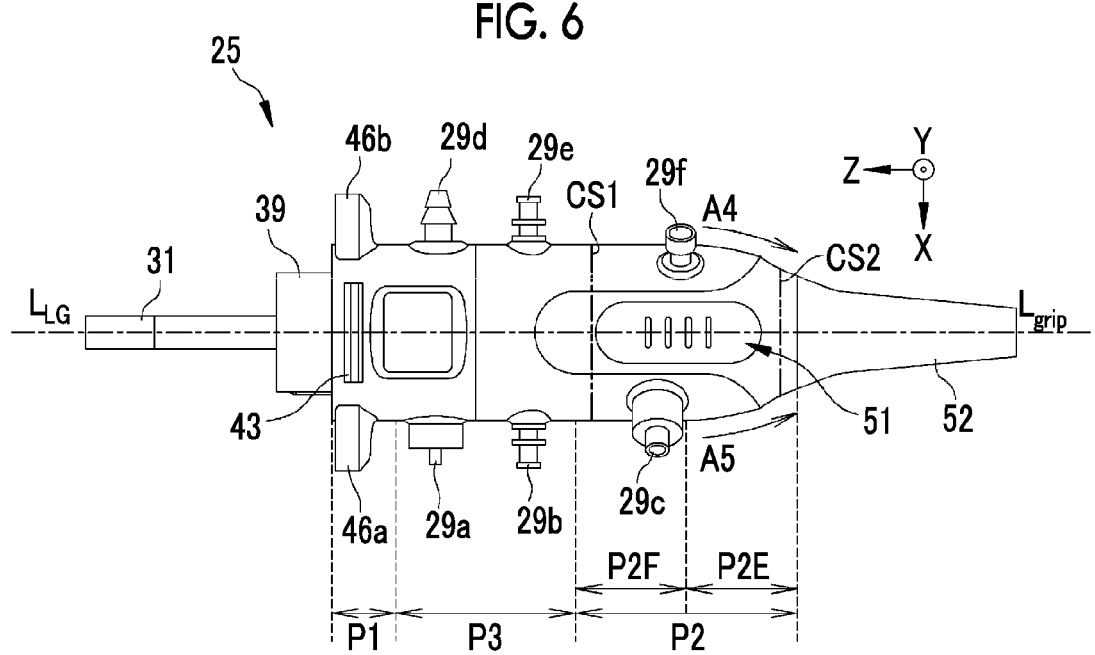
FIG. 6 is a top view of the connector.

In a case in which the connector 25 is viewed from the upper surface 41, the central axis $L_{grip}$ of the grip section P2 is coincident with the central axis $L_{LG}$ of the light guide part 31 that protrudes from the front surface 32 as shown in FIG. 6. Furthermore, the finger placing portion 51 is formed on the central axis $L_{grip}$ of the grip section P2 in a case in which the connector 25 is viewed from the upper surface 41. Meanwhile, in a case in which the connector 25 is viewed from the left side surface as shown in FIG. 7 or in a case in which the connector 25 is viewed from the right side surface, the central axis $L_{LG}$ of the light guide part 31, which protrudes from the front surface 32, is offset to the upper surface 41 with respect to the central axis $L_{grip}$ of the grip section P2.

In addition, the connection terminal 29c is provided on the right side surface of the grip section P2 and the connection terminal 29f is provided on the left side surface of the grip section P2. The connection terminal 29a, the connection terminal 29b, the connection terminal 29d, and the connection terminal 29e, which are provided on the side surfaces of the connector 25, protrude from the connector 25, which is in the connection posture, in the horizontal direction (toward the positive side or the negative side in the X direction), and the connection terminals 29c and 29f, which are provided on the side surfaces of the grip section P2, protrude from the side surfaces of the grip section P2 so as to be inclined toward the upper surface 41 from the horizontal direction by an angle φ (see FIG. 2). Meanwhile, the connection terminal 29a is a tank connector connected to a water supply tank, the connection terminal 29c is a ventilation connector, the connection terminal 29d is a suction connector, and the connection terminal 29f is an S connector to which an S cord is connected when a high-frequency treatment tool such as an electric scalpel is used.

The intermediate section P3 is a portion that connects the housing section P1 to the grip section P2. The shape of a portion of the intermediate section P3 close to the grip section P2 corresponds to the shape of the grip section P2, and the shape of a portion of the intermediate section P3 close to the housing section P1 corresponds to the shape of the housing section P1. Since the cross-section of the housing section P1 has a substantially hog-backed shape and the cross-section of the grip section P2 has a substantially circular shape, the intermediate section P3, which connects the housing section P1 to the grip section P2, has a shape that is smoothly changed to a hog-backed shape from a circular shape toward the housing section P1 from the grip section P2. For this reason, the upper surface 41 of the intermediate section P3 swells to the positive side in the Y direction toward the housing section P1 from the grip section P2 as shown in FIG. 7 by an arrow A8. Further, the lower surface 42 of the intermediate section P3 includes a finger locking portion 61 that is concave to the positive side in the Y direction toward the housing section P1 from the grip section P2 as shown by an arrow A9. The finger locking portion 61 is provided at a portion between the housing section P1 and the grip section P2 where a forefinger reaches in a case in which the connector 25 is gripped at the grip section P2; and locks the forefinger on the lower surface 42 in the connection posture and on the rear of the wireless power receiving unit 34. The finger locking portion 61 includes an inclined surface 62 that is inclined with respect to the central axis $L_{grip}$ of the grip section P2, and the inclined surface 62 is a curved surface of which the inclination angle with respect to the central axis $L_{grip}$ of the grip section P2 is gradually increased toward the housing section P1 from the grip section P2.

Since the forefinger is locked to the finger locking portion 61 when a user naturally grips the connector 25, the forefinger is always spaced apart from the wireless power receiving unit 34 by a predetermined distance. For this reason, the wireless power receiving unit 34 is heated when receiving power supplied from the light source device 14, but it is possible to prevent the forefinger from coming into contact with the vicinity of the heated wireless power receiving unit 34 since the finger locking portion 61 is provided. Therefore, it is possible to safely remove the connector 25 from the light source device 14.

Figure 9:
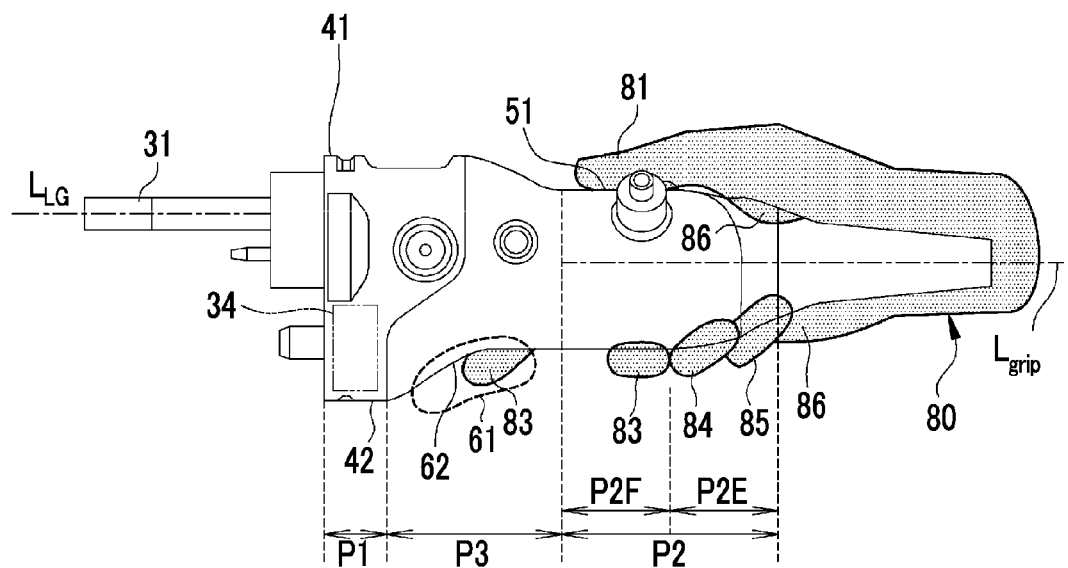
FIG. 9 is a side view of the connector that is gripped with the right hand.

When a user grips the connector 25 having the above-mentioned structure with, for example, the right hand 80, the user grips the grip section P2 while placing a thumb 81 on the finger placing portion 51 as shown in FIGS. 8 and 9. In this case, the back, the forefinger 82, a middle finger 83, a ring finger 84, and a little finger 85 of the right hand 80 wrap around the lower surface 42 while coming into contact with the right side surface of the connector 25. Further, the forefinger 82 is placed on the finger locking portion 61 of the intermediate section P3 and the thumb 81, the middle finger 83, the ring finger 84, the little finger 85, and a carpal region 86 grip the grip section P2. That is, since the grip section P2 of the connector 25 can be "gripped" by substantially the entire right hand 80, the connector 25 can be stably gripped and is easily connected to the light source device 14.

Particularly, when the thumb 81 is placed on the finger placing portion 51, the connector 25 is substantially naturally gripped as described above. Accordingly, the posture of the connector 25, which is gripped, naturally becomes the connection posture. For this reason, since the finger placing portion 51 is provided on the upper surface 41 of the grip section P2, the connector 25 is more easily gripped and connected to the light source device 14 than a connector of an endoscope in the related art.

Furthermore, the cross-section of the grip section P2, which is perpendicular to the central axis $L_{grip}$, has a substantially circular shape regardless of a position in the Z direction; the front portion P2F, which is close to the housing section P1, of the grip section P2 has a substantially constant cross-sectional area; and the cross-sectional area of the rear portion P2E is reduced toward the rear end of the connector 25 that is positioned on the negative side in the Z direction where the universal cable 23 is provided. Accordingly, the grip of the connector fits the above-mentioned grip. For this reason, the connector 25 has a shape that is particularly easily gripped and is easily connected to the light source device 14.

In addition, in a case in which a user grips the grip section P2 by substantially the entire right hand 80 while placing the thumb 81 on the finger placing portion 51, an axis of a connection operation for moving the gripped connector 25 to the light source device 14 is hardly shaken when the user additionally places the forefinger 82 on the finger locking portion 61. For this reason, the finger locking portion 61, which is formed on the lower surface 42 of the intermediate section P3, also improves stability during the gripping of the connector 25 and the stability of the connection operation for moving the connector 25 to the light source device 14.

Moreover, since the upper surface 41 of the housing section P1 is formed of a curved surface having the shape of a circular arc, it is easy to connect the connector 25 to the light source device 14. Specifically, since a vertex of the housing section P1 that seems to most protrude, a sensory central axis ($L_{grip}$) of the right hand 80 that grips the connector 25, and the light guide part 31 are lined up on a line when a user grips the connector 25 and views the upper surface 41 of the housing section P1, there is a sense of unity as a whole. For this reason, since the sense of position of the light guide part 31 does not deteriorate according to an angle at which a user views the connector 25, or the like, the connector 25 is easily connected to the light source device 14. Meanwhile, since the upper surface 41 of the housing section P1 is formed of a curved surface having the shape of a circular arc, the housing section P1 saves space in comparison with a case in which the housing section P1 is formed in a rectangular parallelepiped shape.

A sense of direction in a case in which a user grips the connector 25 depends on the direction of the thumb 81 that is placed on the finger placing portion 51. The connector 25 allows the central axis $L_{LG}$ of the light guide part 31 to be offset to the upper surface 41 with respect to the central axis $L_{grip}$ of the grip section P2 so that the central axis $L_{LG}$ of the light guide part 31 is close to the thumb 81. For this reason, since it is possible to more correctly grasp the position of the light guide part 31 than a case in which the central axis $L_{LG}$ of the light guide part 31 is distant from the thumb 81, the connector 25 is easily connected to the light source device 14. Further, since the central axis $L_{LG}$ of the light guide part 31 is offset to the upper surface 41 in the connector 25, a space, which is used to form the finger locking portion 61, is provided on the lower surface 42 of the intermediate section P3. For this reason, the offset of the central axis $L_{LG}$ of the light guide part 31 to the upper surface 41 also contributes to the ease of the grip of the connector 25.

A sense of direction of the right hand 80, which grips the connector 25, also depends on the center of the grip, that is, the central axis $L_{grip}$ of the grip section P2. Since the central axis $L_{grip}$ of the grip section P2 is coincident with the central axis $L_{LG}$ of the light guide part 31, which protrudes from the front surface 32, in a case in which the connector 25 is viewed from the upper surface 41, the sense of direction of the right hand 80, when the connector 25 is gripped, corresponds to the direction of the light guide part 31 (the central axis $L_{LG}$). For this reason, the connector 25 is easily connected to the light source device 14.

Further, since the finger placing portion 51 is formed on the central axis $L_{grip}$ of the grip section P2 in a case in which the connector 25 is viewed from the upper surface 41, the direction of the thumb 81, which grips the connector 25, naturally becomes parallel to the central axis $L_{grip}$ of the grip section P2. For this reason, since the direction of the light guide part 31 is easily determined, the connector 25 is easily connected to the light source device 14. Furthermore, since the finger placing portion 51 is formed of a stadium-shaped recess of which the length Wz in a direction (the first direction) parallel to the central axis $L_{grip}$ of the grip section P2 is longer than the length Wx in a direction (the second direction) orthogonal to the central axis $L_{grip}$ of the grip section P2, the direction of the thumb 81 is likely to naturally become parallel to the central axis $L_{grip}$ of the grip section P2. Accordingly, the shape of the finger placing portion 51 allows the connector 25 to be easily connected.

Meanwhile, since the connection terminals 29c and 29f, which are provided on the side surfaces of the grip section P2, of the connector 25 protrude from the side surfaces of the grip section P2 so as to be inclined toward the upper surface 41 from the horizontal direction by an angle φ (see FIG. 2), the connection terminals 29c and 29f do not hinder a user from gripping the grip section P2 with the right hand 80 or the left hand when the user grips the connector 25. That is, the inclination of the connection terminals 29c and 29f, which are provided on the side surfaces of the grip section P2, from the horizontal direction allows the user to easily grip the connector 25. The connection terminal 29c has been provided on the left side surface of the grip section P2 of the connector 25 and the connection terminal 29f has been provided on the right side surface thereof, but only one of the connection terminals 29c and 29f may be provided or a plurality of connection terminals may be provided on one side surface so as to be inclined toward the upper surface 41.

Figure 10:
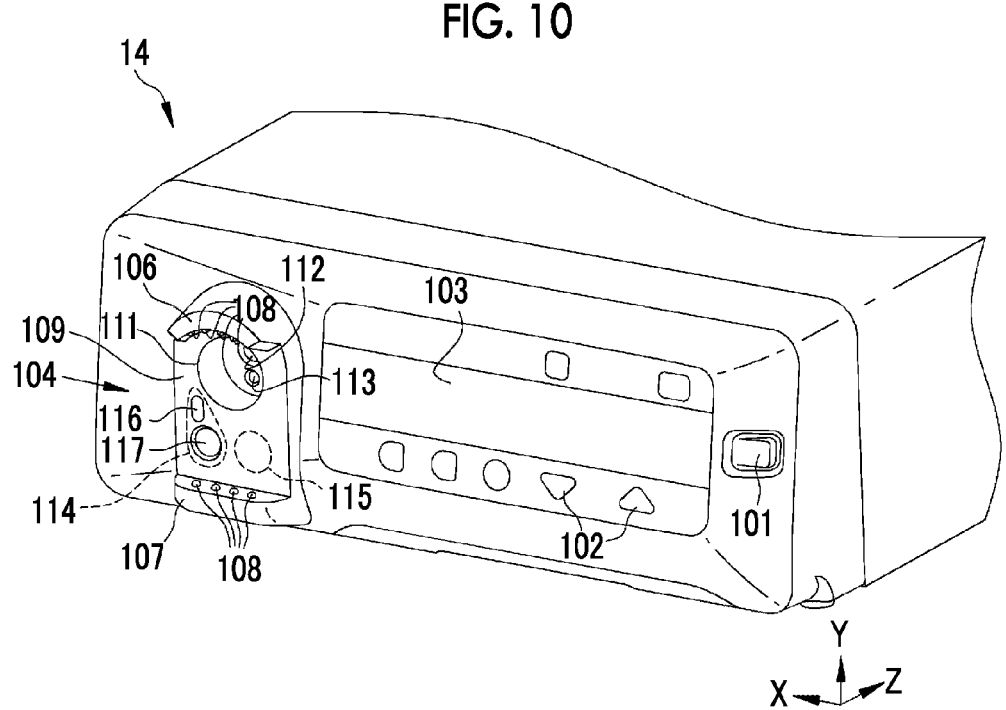
FIG. 10 is a perspective view of a light source device.

Meanwhile, as shown in FIG. 10, a power button 101, operation buttons 102, and a display panel 103 are provided on the front surface of the light source device 14 and a connection section 104 to which the connector 25 is connected is provided on the right side of the front surface (the positive side in the X direction). The connection section 104 includes an upper flange portion 106 and a lower flange portion 107 that are provided at positions corresponding to the upper surface 41 and the lower surface 42 of the connector 25 and protrude from the front surface of the light source device 14 toward the negative side in the Z direction. Since the light source device 14 locks the upper and lower surfaces 41 and 42 of the housing section P1 by the upper and lower flange portions 106 and 107 of the connection section 104 when the connector 25 is connected to the light source device 14, the light source device 14 maintains connection between the connector 25 and itself. For this purpose, the locking members 108, which lock the connector 25, are provided on the inner surface of the upper flange portion 106 that comes into contact with the upper surface 41 of the connector 25 and the inner surface of the lower flange portion 107 that comes into contact with the lower surface 42 of the connector 25. The upper and lower flange portions 106 and 107 of the connection section 104 are holding portions that hold the connector 25 connected to the connection section 104. Further, since the upper flange portion 106 has the shape of a curved surface corresponding to the upper surface 41 of the housing section P1 and the lower flange portion 107 has the shape of a flat surface corresponding to the lower surface 42 of the housing section P1, the upper and lower flange portions 106 and 107 also function as a connection guide portion that guides the connector 25 in a correct connection posture. The lower surface 42 of the housing section P1 of the connector 25 is a flat surface and the lower flange portion 107 of the connection section 104 corresponding to the lower surface 42 supports the connector 25 by a flat surface. Accordingly, even though the universal cable 23 moves and a twisting force is applied around the central axis $L_{LG}$ of the light guide part 31, the connection section 104 stably holds the connector 25 without the application of a load to the light guide part 31 and the like.

The fitting recess 111 to which the fitting protrusion 39 of the connector 25 is fitted is formed on a front surface (hereinafter, referred to as a contact surface) 109 coming into contact with the front surface 32 of the connector 25, and a first hole portion 112 into which the light guide part 31 of the connector 25 is inserted and a second hole portion 113 into which the pump connection portion 38 is inserted are further formed in the fitting recess 111.

Furthermore, a wireless communication unit 114 that wirelessly communicates with the wireless communication unit 33 of the connector 25 and a wireless power supply unit 115 that supplies power to the wireless power receiving unit 34 of the connector 25 are provided on the rear of a lower portion of the contact surface 109. The wireless communication unit 114 includes: a control signal sending/receiving part 116 that sends and receives control signals to and from the control signal sending/receiving part 36; and an image signal receiving part 117 that receives image signals from the image signal sending part 37. A connection terminal of the control signal sending/receiving part 116 is formed substantially on the contact surface 109, and a connection terminal of the image signal receiving part 117 is formed of a hole portion into which the image signal sending part 37 is inserted. The wireless power supply unit 115 is, for example, a coil (a so-called primary coil), and supplies power to the wireless power receiving unit 34 by a non-contact power transmission method, such as an electromagnetic induction method or a magnetic field resonance method.

Figure 11:
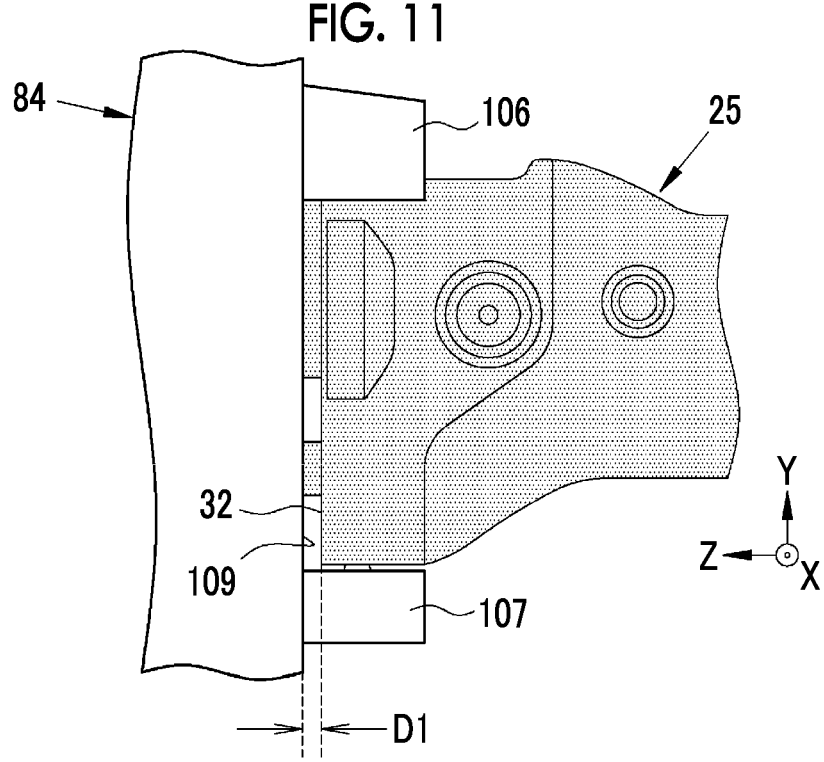
FIG. 11 is a side view of a connection section to which the connector is connected.

The positions of the locking members 108 and the grooves 43 and 44 to which the locking members 108 are fitted are determined so that a gap D1 is formed between the front surface 32 of the connector 25 and the contact surface 109 of the connection section 104 when the connector 25 is connected to the connection section 104 as shown in FIG. 11. When dust or the like is present between the wireless power supply unit 115 and the wireless power receiving unit 34 during the supply of power to the wireless power receiving unit 34 from the wireless power supply unit 115, the dust or the like may generate heat. However, since the gap D1 is formed between the front surface 32 and the contact surface 109, it is possible to prevent dust or the like from being interposed between the wireless power supply unit 115 and the wireless power receiving unit 34 and to safely supply power to the wireless power receiving unit 34 from the wireless power supply unit 115.

Figure 12:
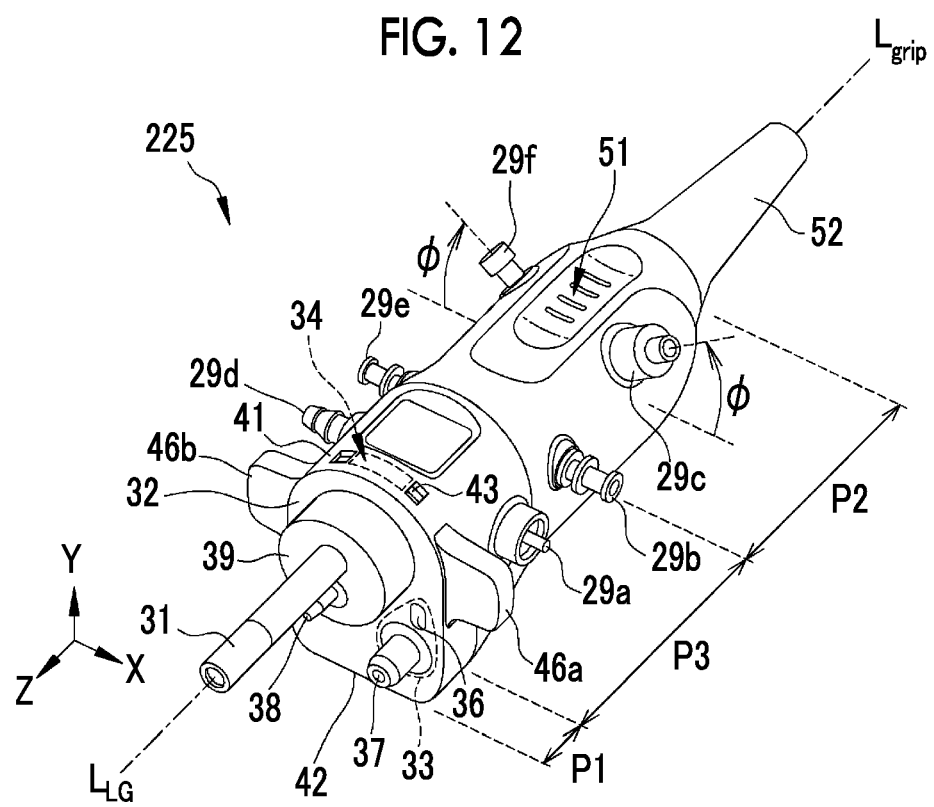
FIG. 12 is a perspective view of the connector that includes a wireless power receiving unit on the upper surface thereof.

Meanwhile, in the above-mentioned embodiment, the housing section P1 of the connector 25 has housed the wireless power receiving unit 34 on the rear of the front surface 32 so that the wireless power receiving unit 34 comes into contact with the front surface 32. However, instead of this, as in a connector 225 shown in FIG. 12, a housing section P1 may house a wireless power receiving unit 34 so that a wireless power receiving unit 34 comes into contact with an upper surface 41, and the wireless power receiving unit 34 may receive power supplied from the upper surface 41. In this case, the connection section 104 of the light source device 14 includes the wireless power supply unit 115 on the upper flange portion 106, and power is supplied to the wireless power receiving unit 34 from the wireless power supply unit 115 through the upper flange portion 106.

Figure 13:
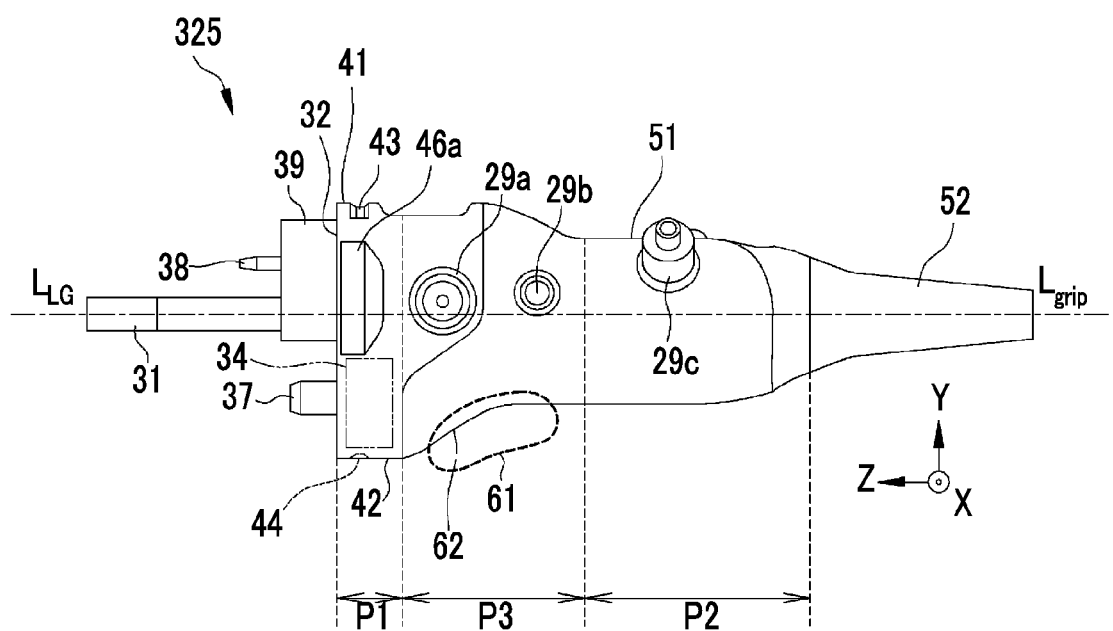
FIG. 13 is a side view of the connector of which the central axis of a light guide part and the central axis of a grip section are coincident with each other.

In the above-mentioned embodiment, in a case in which the connector 25 is viewed from the left side surface or in a case in which the connector 25 is viewed from the right side surface, the central axis $L_{LG}$ of the light guide part 31, which protrudes from the front surface 32, has been offset to the upper surface 41 with respect to the central axis $L_{grip}$ of the grip section P2. However, as in a connector 325 shown in FIG. 13, the central axis $L_{LG}$ of the light guide part 31, which protrudes from the front surface 32, may be made to be coincident with the central axis $L_{grip}$ of the grip section P2 by the change of the disposition or the like of the pump connection portion 38 and the light guide part 31.

What is claimed is:

1. A connector for an endoscope that is connected to a light source device generating illumination light, the connector comprising:
   a light guide part that guides the illumination light;
   a wireless communication unit that wirelessly communicates with the light source device;
   a wireless power receiving unit that receives power wirelessly supplied from the light source device;
   a housing section which houses the wireless communication unit and the wireless power receiving unit and in which the light guide part protrudes from a front surface of the housing section, wherein the front surface is positioned adjacent to the light source device in a connection posture where the connector is connected to the light source device; and
   a grip section that includes a concave finger placing portion on which a thumb is placed, wherein the concave finger placing portion is vertically aligned with a central axis of the light guide part in a case in which the grip section is viewed from above an upper surface of the connector, and the upper surface is positioned on a vertically upper side in the connection posture.

2. The connector according to claim 1,
   wherein a central axis of the grip section is coincident with the central axis of the light guide part in a case in which the connector is viewed from above the upper surface in the connection posture.

3. The connector according to claim 1,
   wherein the central axis of the light guide part is offset to the upper surface of the connector in the connection posture with respect to a central axis of the grip section.

4. The connector according to claim 2,
   wherein the central axis of the light guide part is offset to the upper surface of the connector in the connection posture with respect to the central axis of the grip section.

5. The connector according to claim 3,
   wherein the housing section is capable of housing the wireless communication unit and the wireless power receiving unit on a side of the housing section that is closer to a lower surface of the connector than to the upper surface of the connector, wherein the lower surface is opposite to the upper surface and is positioned on a vertically lower side in the connection posture.

6. The connector according to claim 1,
   wherein the grip section comprises a rear portion opposite to the housing section and a front portion closer to the housing section than the rear portion, and the grip section has a shape in which a cross-sectional area decreases toward the rear portion from the front portion in the connection posture.

7. The connector according to claim 2,
   wherein the grip section comprises a rear portion opposite to the housing section and a front portion closer to the housing section than the rear portion, and the grip section has a shape in which a cross-sectional area decreases toward the rear portion from the front portion in the connection posture.

8. The connector according to claim 3,
   wherein the grip section comprises a rear portion opposite to the housing section and a front portion closer to the housing section than the rear portion, and the grip section has a shape in which a cross-sectional area decreases toward the rear portion from the front portion in the connection posture.

9. The connector according to claim 4,
wherein the grip section comprises a rear portion opposite to the housing section and a front portion closer to the housing section than the rear portion, and the grip section has a shape in which a cross-sectional area decreases toward the rear portion from the front portion in the connection posture.

10. The connector according to claim 1,
wherein a lower surface of the housing section, which is positioned on a vertically lower side in the connection posture, is a flat surface.

11. The connector according to claim 2,
wherein a lower surface of the housing section, which is positioned on a vertically lower side in the connection posture, is a flat surface.

12. The connector according to claim 3,
wherein a lower surface of the housing section, which is positioned on a vertically lower side in the connection posture, is a flat surface.

13. The connector according to claim 5,
wherein a lower surface of the housing section, which is positioned on the vertically lower side in the connection posture, is a flat surface.

14. The connector according to claim 6,
wherein a lower surface of the housing section, which is positioned on a vertically lower side in the connection posture, is a flat surface.

15. The connector according to claim 1,
wherein an upper surface of the housing section, which is positioned on the vertically upper side in the connection posture, is a curved surface.

16. The connector according to claim 1,
wherein the wireless communication unit is capable of performing near-infrared communication between the light source device and itself.

17. The connector according to claim 1,
wherein a front surface of the connector where the wireless power receiving unit receives power supplied from the light source device has a structure in which a gap is formed between the front surface of the connector and a contact surface of the light source device in a case in which the connector is connected to the light source device.

18. The connector according to claim 1,
wherein the housing section houses the wireless power receiving unit so that the wireless power receiving unit comes into contact with the upper surface of the connector in the connection posture, and
the wireless power receiving unit is capable of receiving power supplied from the light source device through the upper surface of the connector in the connection posture.

19. The connector according to claim 18,
wherein in a case in which the light source device includes an upper flange portion that holds the upper surface of the connector in the connection posture, the wireless power receiving unit is capable of receiving power to be supplied through the upper flange portion.

20. The connector according to claim 1,
wherein the central axis of the light guide part is coincident with the central axis of the grip section in a case in which the connector is viewed from a left side or a right side in the connection posture.

* * * * *